United States Patent [19]
Blank et al.

[11] Patent Number: 5,484,800
[45] Date of Patent: Jan. 16, 1996

[54] LIPID-BASED LIQUID MEDICINAL COMPOSITION

[75] Inventors: Robert G. Blank, Hammonton; Annabelle Mogavero, Marlton; Alexander Seabrook, Sicklerville, all of N.J.

[73] Assignee: American Home Products Corporation, Madison, N.J.

[21] Appl. No.: 300,013

[22] Filed: Aug. 30, 1994

[51] Int. Cl.$^6$ .................. A61K 31/34; A61K 31/425
[52] U.S. Cl. .................. 514/365; 514/370; 514/400; 514/471; 514/770; 514/785; 514/786; 514/926
[58] Field of Search .................. 514/365, 370, 514/400, 471, 770, 785, 786, 926

[56] References Cited

U.S. PATENT DOCUMENTS 4,980,175  12/1990  Chavkin et al. .................. 424/677

*Primary Examiner*—Richard L. Raymond
*Attorney, Agent, or Firm*—S. H. Flynn

[57] ABSTRACT

The present invention is directed to liquid medicinal suspension compositions for the administration of doses of active pharmaceutical agents such as $H_2$-antagonists. $H_2$-antagonists are known for their adverse taste and/or malodor and the claimed suspension functions to mask the adverse taste and odor of such active ingredients. Also disclosed are liquid medicinal compositions comprising the claimed suspension composition and the $H_2$-antagonist active ingredients.

20 Claims, No Drawings

LIPID-BASED LIQUID MEDICINAL COMPOSITION

FIELD OF THE INVENTION

The present invention is directed to lipid-based, liquid medicinal suspension compositions for the administration of $H_2$-receptor antagonists which are known for their adverse taste and/or malodor. The present invention is further directed to liquid medicinal compositions comprising the claimed suspension compositions and such $H_2$-receptor antagonists.

BACKGROUND OF THE INVENTION $H_2$-receptor antagonists (hereinafter referred to $H_2$-antagonists) are characterized as a family by their ability to inhibit the secretion of gastric acid. They are currently prescribed for the treatment of duodenal ulcers as well as other hypersecretory states. Prior to FDA approval of these compounds, the mainstay of therapy in the reduction of gastric acidity involved the neutralization of gastric acid with conventional antacids.

One of the chief complaints associated with administration of $H_2$-antagonists is their adverse taste and/or malodor. Many attempts have been made in developing delivery systems for these compounds with varying degrees of success.

U.S. Pat. No. 4,980,175 discloses an orally ingestible liquid composition for suspending therein high concentrations of at least one orally administrable pharmaceutically active agent. The composition is said to comprise (a) about 40 to about 70 parts by weight of a member of the group consisting of at least one triglyceride or propylene glycol ester of a medium chain length alkanoic acid, wherein at least 95% by weight of the said acid has between 8 and 10 carbon atoms in the chain and at least one acetylated monoglyceride of at least one medium chain length alkanoic acid, having hydroxyl value of 0–15, an acetylation level of at least 95% and a melting point between about 4° and about 12° C., (b) about 2 to about 15 parts by weight of a polyglycerol ester, liquid at least 20° C. and having an HLB of at least 8.0, (c) about 1 to about 5 parts by weight of colloidal silicon dioxide to a total of between about 50 and about 90 parts by weight.

As stated above, the composition of U.S. Pat. No. 4,980,175 is said to permit fluid suspensions containing relatively high concentrations of pharmaceutically active agents. Disclosed therein are compositions of containing 20% by weight of calcium polycarbophil and 30% by weight of conventional antacids.

Surprisingly, it has been found that the suspension vehicle similar to that of U.S. Pat. No. 4,980,175 serves as a satisfactory vehicle for the administration of $H_2$-antagonists. The polyglycerol ester component of the fluid suspensions, disclosed as necessary in U.S. Pat. No. 4,980,175, may be omitted. When used in conjunction with $H_2$-antagonists as active components, such suspension vehicles function well in controlling the objectional taste and malodor of the active component. Further, the absence of the polyglycerol ester component required in the formulations of U.S. Pat. No. 4,980,175 has been found to also offer the benefits of (a) absence of the mildly objectional taste of the polyglycerol ester itself, and (b) the ability of the suspension to suspend additional quantities of active component.

SUMMARY OF THE INVENTION

The present invention is directed to an improved orally ingestible liquid composition for suspending therein at least one orally administrable pharmaceutically active compound. As stated above, said composition comprises (a) about 95 to about 99 parts by weight of at least one triglyceride or propylene glycol ester of a medium chain length alkanoic acid wherein said acid has between 8 and 10 carbon atoms in the chain or at least one acetylated monoglyceride of at least one medium chain length alkanoic acid having a hydroyxl value of 0– 15, an acetylation level of at least 95% and a melting point between about 4° and about 12° C., and (b) about 1 to about 5 parts by weight of colloidal silicon dioxide to a total of between about 50 and about 90 parts by weight.

The present invention is further directed to an improved orally ingestible liquid pharmacuetical composition which comprises (a) about 85 to about 99 parts by weight of at least one triglyceride or propylene glycol ester of a medium chain length alkanoic acid wherein said acid has between 8 and 10 carbon atoms in the chain or at least one acetylated monoglyceride of at least one medium chain length alkanoic acid having a hydroyxl value of 0– 15, an acetylation level of at least 95% and a melting point between about 4° and about 12° C., (b) about 0.5 to about 5 parts by weight of colloidal silicon dioxide to a total of between about 50 and about 90 parts by weight, and (c) about 0.2 to about 10 parts by weight of an $H_2$-antagonist.

DESCRIPTION OF THE INVENTION

As stated above, there is provided an improved orally ingestible liquid composition for suspending therein at least one orally administrable pharmaceutically active compound. As stated above, said composition comprises (a) about 95 to about 99 parts by weight of at least one triglyceride or propylene glycol ester of a medium chain length alkanoic acid wherein said acid has between 8 and 10 carbon atoms in the chain or at least one acetylated monoglyceride of at least one medium chain length alkanoic acid having a hydroyxl value of 0– 15, an acetylation level of at least 95% and a melting point between about 4° and about 12° C., and (b) about 0.5 to about 5 parts by weight of colloidal silicon dioxide to a total of between about 50 and about 90 parts by weight.

The present invention is further directed to an improved orally ingestible liquid pharmacuetical composition which comprises (a) about 85 to about 99 parts by weight of at least one triglyceride or propylene glycol ester of a medium chain length alkanoic acid wherein said acid has between 8 and 10 carbon atoms in the chain or at least one acetylated monoglyceride of at least one medium chain length alkanoic acid having a hydroyxl value of 0– 15, an acetylation level of at least 95% and a melting point between about 4° and about 12° C., (b) about 0.5 to about 5 parts by weight of colloidal silicon dioxide to a total of between about 50 and about 90 parts by weight, and (c) about 0.2 to about 10 parts by weight of an $H_2$-antagonist.

Preferably, the alkanoic acid moiety of component (a) above, namely the triglyceride or propylene glycol ester of the medium chain length alkanoic acid component, is caprylic acid or capric acid.

Commercially available examples of component (a) are medium chain triglycerides such as Neobee® O and Neobee® M5, manufactured by PVO International; Miglycol® 810, 812, 818, 829 and 840, manufactured by Dynamit Nobel; Captex® 200, 300, 350, 355 and 810B, manufactured by Capital City Products and acelylated monoglycerides such as Myvacet® 9-45K, manufactured by Eastman Kodak. Particularly preferred is the use of a medium chain triglyceride containing approximately 66% caprylic acid, 31% capric acid, 2% caproic acid and 1% lauric acid which is marketed by Karlshamns Lipid Specialties USA under the tradename Captex® 300.

Component (a) is typically present in amounts ranging from about 95 to about 99 weight percent, based on the total weight of the suspension vehicle. Preferably, Component (a) is present in amounts ranging from about 98 to about 99 weight percent, based on the total weight of the suspension vehicle. Most preferably, Component (a) is present in an amount of about 99 weight percent, based on the total weight of the suspension vehicle. However, it should be noted that the amount of Component (a) may be reduced significantly if significant quantities of optional components such as sweeteners are added to the composition. In such case, the amount of Components (a) present in the final composition may be as low as about 65 weight percent, based on the total weight of the suspension vehicle.

Component (b) is typically present in amounts ranging from about 0.5 to about 5 weight percent, based on the total weight of the suspension vehicle. The silicon dioxide component is preferably hydrophilic fumed silicon dioxide. Preferably, Component (b) is present in amounts ranging from about 1 to about 2 weight percent, based on the total weight of the suspension vehicle. Most preferably, Component (b) is present in an amount of about 1 weight percent, based on the total weight of the suspension vehicle.

It is to be further understood in the art that the suspending composition may be employed in conjunction with any orally administratable pharmaceutically active agents. The class of orally administrable pharmaceutically active compounds useful in the practice of the present invention is not narrowly critical. Their use is permissible so long as no undue degradation of such active compounds occurs or undesirable byproducts are produced due to contact with the claimed suspension vehicle. Preferred in the practice of the present invention is the use of $H_2$-antagonists. These include ranitidine, cimetidine, nizatidine and famitodine.

The $H_2$-antagonists are typically present in amounts ranging from about 0.2 to about 10 weight percent, based on the total weight of the composition (suspension vehicle plus $H_2$-antagonist). Preferably, these compounds are present in amounts ranging from about 0.4 to about 6 weight percent, based on the same basis. Most preferably, these compounds are present in an amount of about 1.5 weight percent, on the same basis.

The claimed orally ingestible liquid pharmacuetical composition may optionally contain conventional antacids such as those recognized in the official FDA final monograph on antacids as part of their OTC Drug review published in 1981. These include basic aluminum salts, particularly aluminum hydroxide, dried gel USP basic magnesium salts, i.e., magnesium trisilicate USP, magnesium hydroxide USP, magnesium oxide USP and magnesium carbonate USP, basic calcium salts, particularly calcium carbonate USP, basic sodium or potassium salts, particularly sodium or potassium bicarbonate. These materials may generally be present in amounts ranging from about 2.5 to about 10 weight percent, based on the weight of the final composition.

In addition to the essential ingredients described above, the claimed compositions may contain other ingredients such as flavors, colors, natural and artificial sweeteners, preservatives antiflatulent additives (e.g. simethicone).

The following Examples are offered to illustrate the practice of the present invention. They should not be construed as a limitation on the scope of such invention or its practice.

EXAMPLES

Example 1

The following compositions are placed in a suitable vessel:

a. 250 grams of confectioners sugar (supplied by Domino Sugar Corp.);

b. 20 grams of colloidal silicon dioxide (supplied by the Cabot Corporation);

c. 20 grams of aspartame (supplied by the Nutrasweet Company);

d. 20 grams of a sweetener sold by the Mac Andrew and Forbes Company under the tradename Mafco Magnasweet 135; and e. 250 grams of fructose powder (supplied by Crompton & Knowles).

These materials are mixed/blended for several minutes until uniformly dispersed. If necessary, the mixture (or individual components prior to their addition) may be passed through a fine mesh sieve to break up any lumps present.

A medium chain triglyceride containing approximately 66% caprylic acid, 31% capric acid, 2% caproic acid and 1% lauric acid (marketed by Karlshamns Lipid Specialties USA under the tradename CAPTEX 300) in an amount of about 1000 grams is introduced into a a mixing vessel having a volume greater than 2 liters, calibrated to 2 liters and equipped with a Lightin® mixer. This material is mixed for a suitable time. The mixed materials (a)–(e) are then introduced into the mixing vessel and mixing is continued.

Nizatidine (supplied in bulk by Eli Lilly and Company) in an amount of about 30 grams is then introduced into the mixer. Mixing is continued.

Additional quantities of the medium chain triglyceride are then added until the final volume of the mixture equals 2 liters. Mixing is continued for about 2 hours after completion of the final addition.

The suspension produced is found to effectively mask the offensive taste and malodor of the active component, nizatidine.

Example 2

The following compositions are placed in a suitable vessel:

a. 250 grams of confectioners sugar (supplied by Domino Sugar Corp.);

b. 20 grams of colloidal silicon dioxide (supplied by the Cabot Corporation);

c. 20 grams of aspartame (supplied by the Nutrasweet Company);

d. 20 grams of a sweetener sold by the Mac Andrew and Forbes Company under the tradename Mafco Magnasweet 135; and e. 250 grams of fructose powder (supplied by Crompton & Knowles).

These materials are mixed/blended for several minutes until uniformly dispersed. If necessary, the mixture (or individual components prior to their addition) may be passed through a fine mesh sieve to break up any lumps present.

About 1000 grams of CAPTEX® 300 is introduced into a mixing vessel having a volume greater than 2 liters, calibrated to 2 liters and equipped with a Lightin® mixer. This material is mixed for a suitable time. The mixed materials (a)–(e) are then introduced into the mixing vessel and mixing is continued.

Cimetidine (supplied in bulk by Sigma) in an amount of about 30 grams is passed through a fine mesh screen and is then introduced into the mixing vessel. Mixing is continued.

Additional quantities of the medium chain triglyceride are then added until the final volume of the mixture equals 2 liters. Mixing is continued for about 2 hours after completion of the final addition.

The suspension produced is found to effectively mask the offensive taste and malodor of the active component, cimetidine.

Example 3

The following compositions are placed in a suitable vessel:

a. 250 grams of confectioners sugar (supplied by Domino Sugar Corp.);

b. 20 grams of colloidal silicon dioxide (supplied by the Cabot Corporation);

c. 20 grams of aspartame (supplied by the Nutrasweet Company);

d. 20 grams of a sweetener sold by the Mac Andrew and Forbes Company under the tradename Mafco Magnasweet 135; and e. 250 grams of fructose powder (supplied by Crompton & Knowles).

These materials are mixed/blended for several minutes until uniformly dispersed. If necessary, the mixture (or individual components prior to their addition) may be passed through a fine mesh sieve to break up any lumps present.

About 1000 grams of CAPTEX® 300 is introduced into a mixing vessel having a volume greater than 2 liters, calibrated to 2 liters and equipped with a Lightin® mixer. This material is mixed for a suitable time. The mixed materials (a)–(e) are then introduced into the mixing vessel and mixing is continued.

Ranitidine (supplied in bulk by Sigma) in an amount of about 30 grams is passed through a fine mesh screen and is then introduced into the mixing vessel. Mixing is continued.

Additional quantities of the medium chain triglyceride are then added until the final volume of the mixture equals 2 liters. Mixing is continued for about 2 hours after completion of the final addition.

The suspension produced is found to effectively mask the offensive taste of the active component, ranitidine.

Example 4

A composition is prepared according to the procedure outlined in Example 1 to produce a composition having the following formula:

a. 25 weight percent of confectioners sugar (supplied by Domino Sugar Corp.);

b. 1 weight percent of colloidal silicon dioxide (supplied by the Cabot Corporation);

c. 1 weight percent of aspartame (supplied by the Nutrasweet Company);

d. 1 weight percent of a sweetener sold by the Mac Andrew and Forbes Company under the tradename Mafco Magnasweet 135;

e. 1.5 weight percent of Nizatidine (supplied in bulk by Eli Lilly and Company); and f. the balance of a medium chain triglyceride containing approximately 66% caprylic acid, 31% capric acid, 2% caproic acid and 1% lauric acid (marketed by Karlshamns Lipid Specialties USA under the tradename CAPTEX 300)

We claim:

1. An orally ingestible liquid composition for suspending therein at least one orally administrable pharmaceutically active compound consisting essentially of (a) about 95 to about 99 parts by weight of at least one triglyceride or propylene glycol ester of a medium chain length alkanoic acid wherein said acid has between 8 and 10 carbon atoms in the chain or at least one acetylated monoglyceride of at least one medium chain length alkanoic acid having a hydroxyl value of 0–15, an acetylation level of at least 95% and a melting point between about 4° and about 12° C., and (b) about 1 to about 5 parts by weight of colloidal silicon dioxide to a total of between about 50 and about 90 parts by weight.

2. The composition of claim 1 wherein the alkanoic acid moiety of component (a) is selected from the group consisting of caprylic acid or capric acid.

3. The composition of claim 1 wherein component (a) comprises a triglyceride of an alkanoic acid moiety selected from the group consisting of caprylic acid or capric acid.

4. The composition of claim 1 wherein component (a) comprises about 99 parts by weight of the composition.

5. The composition of claim 1 wherein component (b) comprises hydrophilic fumed silicon dioxide.

6. The composition of claim 5 wherein component (b) comprises from about 1 to about 2 parts by weight of the composition.

7. An orally ingestible liquid pharmacuetical composition which consisting essentially of (a) about 85 to about 99 parts by weight of at least one triglyceride or propylene glycol ester of a medium chain length alkanoic acid wherein said acid has between 8 and 10 carbon atoms in the chain or at least one acetylated monoglyceride of at least one medium chain length alkanoic acid having a hydroyxl value of 0–15, an acetylation level of at least 95% and a melting point between about 4° and about 12° C., (b) about 0.5 to about 5 parts by weight of colloidal silicon dioxide to a total of between about 50 and about 90 parts by weight, and (c) about 0.2 to about 10 parts by weight of an $H_2$-antagonist.

8. The composition of claim 7 wherein the alkanoic acid moiety of component (a) is selected from the group consisting of caprylic acid or capric acid.

9. The composition of claim 7 wherein component (a) comprises a triglyceride on an alkanoic acid moiety selected from the group consisting of caprylic acid or capric acid.

10. The composition of claim 7 wherein component (a) comprises from about 92 to about 98 parts by weight of the composition.

11. The composition of claim 7 wherein component (b) comprises hydrophilic fumed silicon dioxide.

12. The composition of claim 11 wherein component (b) comprises from about 1 to about 2 parts by weight of the composition.

13. The composition of claim 7 wherein the $H_2$-antagonists comprise ranitidine, cimetidine, nizatidine and famitodine.

14. The composition of claim 7 where the $H_2$-antagonists are present in amounts ranging from about 0.4 to about 6 weight percent, based on the total weight of the composition.

15. The composition of claim 14 where the $H_2$-antagonists are present an amount of about 1.5 weight percent, based on the total weight of the composition.

16. The composition of claim 7 wherein the $H_2$-antagonist comprises nizatidine.

17. The composition of claim 16 where the $H_2$-antagonist is present in amounts ranging from about 0.4 to about 6 weight percent, based on the total weight of the composition.

18. The composition of claim 16 where the $H_2$-antagonist is present in amount of about 1.5 weight percent, based on the total weight of the composition.

19. The composition of claim 7 comprising an antacid selected from the group consisting of basic aluminum salts, basic magnesium salts, basic calcium salts, basic sodium salts, basic potassium salts and malgaldrate.

20. The composition of claim 19 wherein the antacids are present in amounts ranging from about 2.5 to about 10 weight percent, based on the weight of the composition.

* * * * *